(12) United States Patent
Banko

(10) Patent No.: US 10,500,319 B2
(45) Date of Patent: *Dec. 10, 2019

(54) SURGICAL HAND PIECE WITH DUAL LUMEN WORK TIP FOR USE WITH INFUSION CANNULA

(71) Applicant: SURGICAL DESIGN CORPORATION, Armonk, NY (US)

(72) Inventor: William Banko, Armonk, NY (US)

(73) Assignee: SURGICAL DESIGN CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/057,653

(22) Filed: Aug. 7, 2018

(65) Prior Publication Data

US 2018/0344909 A1 Dec. 6, 2018

Related U.S. Application Data

(63) Continuation of application No. 14/142,555, filed on Dec. 27, 2013, now Pat. No. 10,166,317, which is a continuation-in-part of application No. 12/215,315, filed on Jun. 26, 2008, now Pat. No. 8,641,658.

(51) Int. Cl.
  *A61M 1/00* (2006.01)
  *A61B 17/34* (2006.01)
  *A61F 9/007* (2006.01)
  *A61B 17/32* (2006.01)

(52) U.S. Cl.
  CPC ....... *A61M 1/0064* (2013.01); *A61B 17/3421* (2013.01); *A61F 9/00745* (2013.01); *A61B 2017/320084* (2013.01); *A61B 2217/005* (2013.01); *A61B 2217/007* (2013.01)

(58) Field of Classification Search
  CPC .... A61B 17/3421; A61B 2017/320084; A61B 2217/005; A61B 2217/007; A61F 9/00745; A61M 1/0064
  See application file for complete search history.

(56) References Cited

U.S. PATENT DOCUMENTS

| | | | |
|---|---|---|---|
| 4,425,115 | A | 1/1984 | Wuchinich |
| 4,504,264 | A | 3/1985 | Kelman |
| 4,551,130 | A | 11/1985 | Herbert |
| 4,735,604 | A | 4/1988 | Watmough |

(Continued)

*Primary Examiner* — Brandy S Lee
(74) *Attorney, Agent, or Firm* — Leason Ellis LLP

(57) ABSTRACT

A surgical hand piece has a source of ultrasonic energy provided to a connecting body having a first passage with one end to receive fluid from a first source and the other end at the connecting body distal end. A work tip has first and second tubes each having at least one opening at its distal end and the proximal end of one or both of the tubes connected to the connecting body distal end to receive the ultrasonic energy and to selectively receive or discharge fluid from either the first or second source as controlled by a valve. A cannula is provided which is adapted to be placed in an opening in the cornea through which the work tip extends during the removal of cataracts from the eye by phacoemulsification. The cannula may be equipped with channels that permit additional infusion of fluid into the eye during the procedure, which infusion also cools the surrounding corneal tissue to protect against heat generated by the ultrasonic vibration of the work tip.

7 Claims, 8 Drawing Sheets

(56) References Cited

U.S. PATENT DOCUMENTS

| | | |
|---|---|---|
| 4,750,902 A | 6/1988 | Wuchinich |
| 5,084,013 A | 1/1992 | Takase |
| 5,248,297 A | 9/1993 | Takase |
| 5,254,082 A * | 10/1993 | Takase ............ A61B 17/320068 604/22 |
| 5,817,099 A | 10/1998 | Skolik et al. |
| 6,007,511 A | 12/1999 | Prywes |
| 6,282,442 B1 | 8/2001 | DeStefano et al. |
| 6,309,347 B1 | 10/2001 | Takashi |
| 6,878,142 B2 | 4/2005 | Lawrence |
| 7,083,589 B2 | 8/2006 | Banko et al. |
| 7,503,895 B2 | 3/2009 | Rabiner |
| 2002/0022796 A1 | 2/2002 | Lawrence et al. |
| 2002/0161326 A1 | 10/2002 | Sussman et al. |
| 2003/0176791 A1 | 9/2003 | Rabiner et al. |
| 2005/0085769 A1 * | 4/2005 | MacMahon ......... A61M 1/0009 604/96.01 |
| 2005/0267400 A1 | 12/2005 | Haarala |
| 2006/0173244 A1 | 8/2006 | Boulais et al. |
| 2008/0044790 A1 | 2/2008 | Fani |

\* cited by examiner

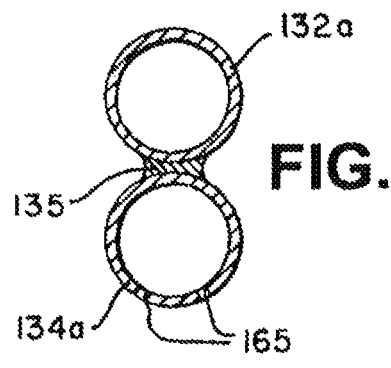
FIG. 3A
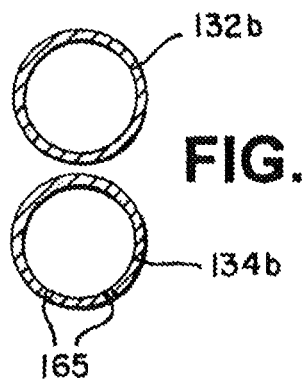
FIG. 3B
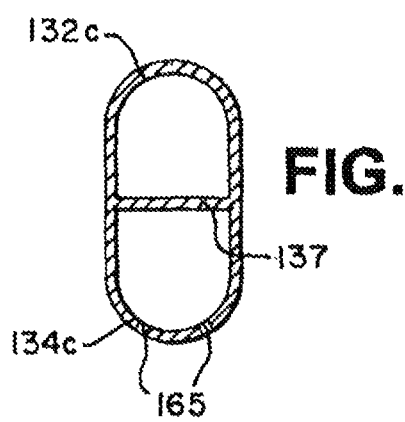
FIG. 3C
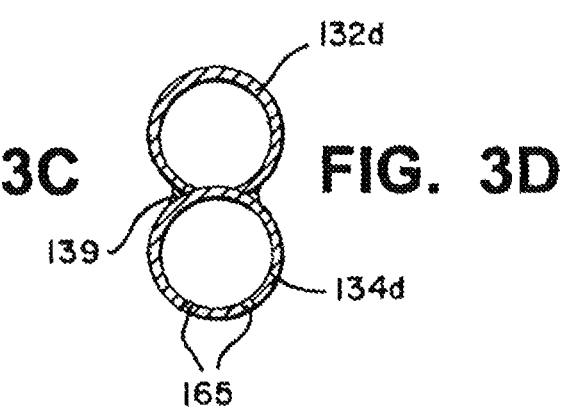
FIG. 3D
FIG. 4A
FIG. 4B
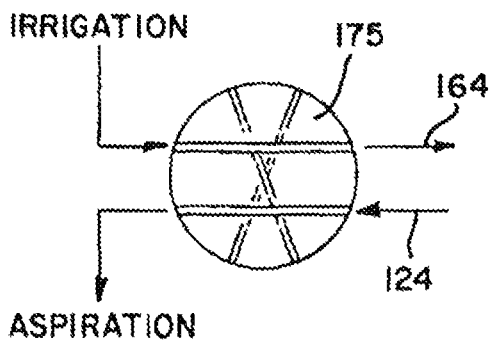
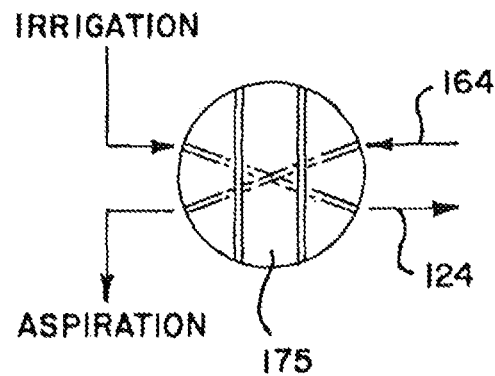

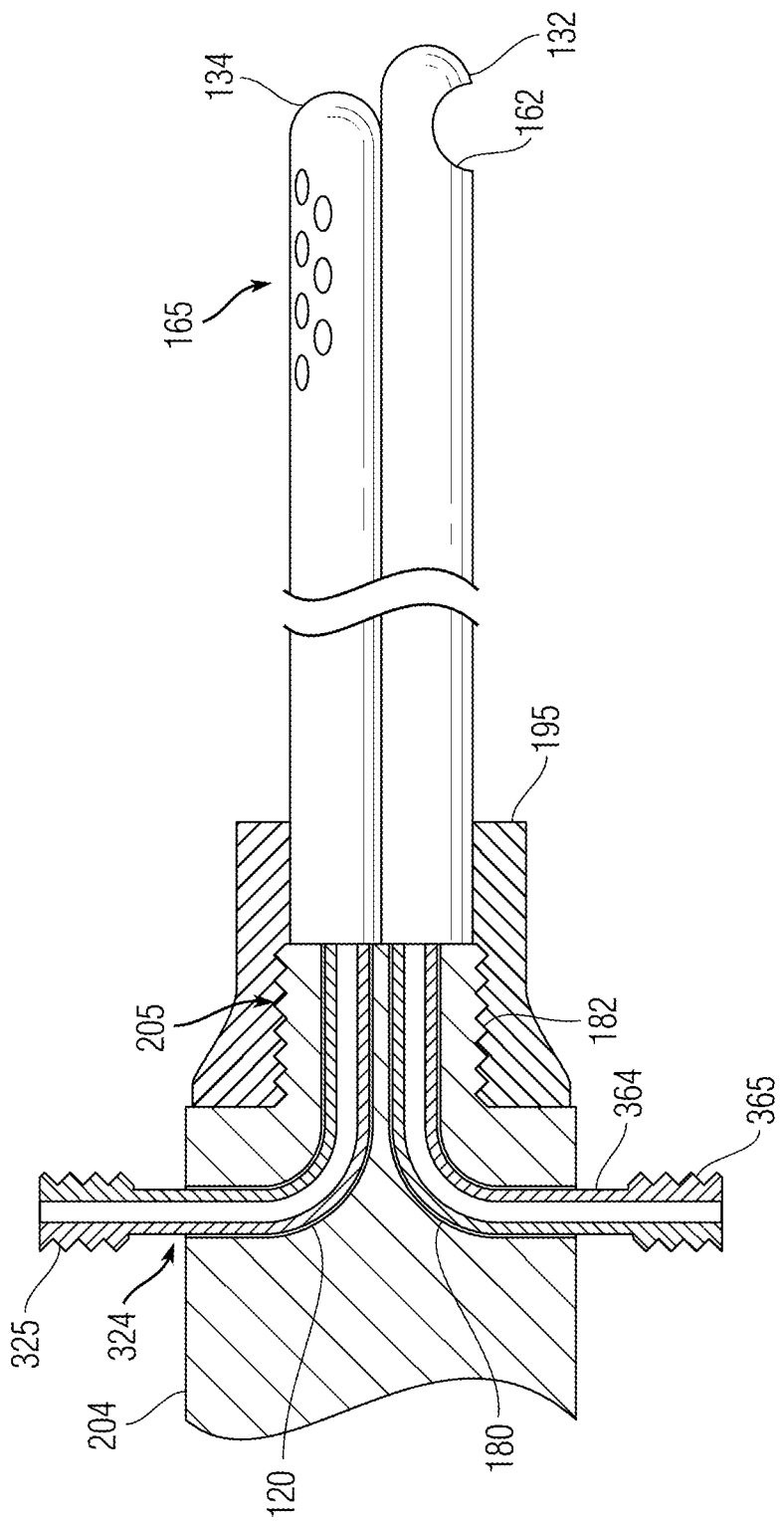

SURGICAL HAND PIECE WITH DUAL LUMEN WORK TIP FOR USE WITH INFUSION CANNULA

CROSS-REFERENCE TO RELATED APPLICATIONS

The present application is a continuation of U.S. application Ser. No. 14/142,555, filed on Dec. 27, 2013, which is a continuation-in-part of prior U.S. patent application Ser. No. 12/215,315 filed on Jun. 26, 2008 (now U.S. Pat. No. 8,641,658, which issued Feb. 4, 2014).

TECHNICAL FIELD

The present invention is generally directed to an ultrasonic surgical hand piece with a dual lumen work tip that is disposable, and can be used for the removal of cataracts from the eye of a patient by phacoemulsification.

BACKGROUND OF THE INVENTION

The use of ultrasonic instruments in surgical applications is well known. One widely used type of instrument is an ultrasonic hand piece that is used in ophthalmic applications, such as in the removal of cataracts from the eye by phacoemulsification.

FIG. 6 depicts one such type of prior art ultrasonic hand piece as shown in U.S. Pat. No. 4,504,264 of Kelman. This hand piece has a housing 10 of, for example, plastic or metal, within which is supported a transducer means 11 for generating mechanical vibrations upon excitation with an alternating-current electrical signal. The transducer 11 is shown as a magnetostrictive transducer with an electrical coil 12 wound about a stack of metal laminations so that longitudinal mechanical vibrations are produced. The transducer can also be of the piezoelectric type. There is a connecting body 16 of, for example, titanium, having a reduced diameter distal end portion, which also can be an attached separate portion. The connecting body forms an acoustic impedance transformer for conveying the longitudinal vibrations of the transducer 11 for application to an operative tool or working tip 14 connected to the distal end of the connecting body 16.

The work tip 14 is at least partially external of the housing 10. It is connected, such as by a screw thread, to the narrowed distal end of the connecting body 16 so as to be coupled to the transducer 11. As a result, the work tip is longitudinally vibrated by the transducer. The working tip 14 is an elongated, hollow tip of a suitable metal, such as titanium, that is capable of supporting ultrasonic vibrations. It has a distal end of a desired shape to be placed against the tissue to be removed. The work tip 14 has a base portion 15 in threaded engagement with the distal end of the connecting body 16. The tip 14 can be interchanged by use of the screw threads.

The distal end of the tip 14 is shown surrounded by a sleeve 17, which may be made of a material such as silicone, whose proximal end 18 is supported in threaded engagement on a reduced diameter end of the housing 10. If desired, the proximal end of sleeve 17 can be engaged more proximally along the length of the housing 10. The connecting body 16 has two elastomeric O-rings 19, 20 on its outer surface. These provide a fluid-tight seal between the connecting body 16 and the transducer means 11. A plurality of screws 51 are shown disposed around the axis of the housing 10 for preventing longitudinal displacement (other than vibration) or rotational movement of the vibratory structure within the housing and also for radial centering of the vibratory structure within the housing. Other types of conventional mounting arrangements can be used.

The hand piece also illustratively has electrical input terminals 40, 41 for applying a suitable electrical signal to the magnetostrictive transducer 11. Cooling water is shown provided inside the housing 10 from an inlet 42 to an outlet 43 and within a chamber between O-ring 19 and a grommet 50 for circulation around the transducer. This is not always necessary and is not used in most present day hand pieces.

The sleeve 17 around the tip 14 forms a first fluid passage 21 between the tip 14 and the sleeve for an irrigation fluid. An inlet 22 is provided on the housing or sleeve distally of the O-ring 20 for supplying the irrigation fluid to the passage 21 from a fluid supply, e.g., a bag of saline solution (not shown).

A passage 23 is formed through the connecting body 16 that is in communication with a central passage 25 of the work tip 14. An outlet 24 on the housing or sleeve receives a suction (aspiration) force that is applied to the passage 23 in the connecting body and the central passage 25 in the work tip. A chamber 31 is formed between the spaced O-rings 19, 20 on the body 16 and the housing 10, with which the aspiration force from outlet 24 communicates. Thus the aspiration force is from the source (e.g., a suction pump not shown), into the chamber 31 between the O-rings, through the passage 23 in the connecting body and the passage 25 in the work tip 14. Tissue that is emulsified by the work tip is aspirated from the operating site by the aspiration flow force. In particular, saline solution introduced into the eye through fluid passage 21 and tissue displaced by the vibration force of the tip 14, is drawn into the distal end of passage 25 and passes out of the hand piece through outlet 24. It should be noted that passage 25 is located concentrically within passage 21.

As indicated, other apparatus (not shown) for use with the hand piece include the suction pump for producing the aspiration fluid (suction), the treatment fluid supply (irrigation fluid, such as a saline liquid), an oscillator for applying an electrical signal to the vibratory structure and control apparatus therefore. All of these are of conventional construction.

Considering now the operation of the hand piece of FIG. 6. When an electrical signal having a frequency of, for example, 40,000 cycles/second is applied to the coil 12 around the magnetostrictive transducer 11, the transducer 11 vibrates longitudinally at 40,000 cycles per second, thereby vibrating the connecting bodies 13, 16 and the work tip 14. Treatment fluid is supplied through inlet 22 and fluid passage 21 to bathe the tissue in the operating site region around the working tip 14. Suction force is applied through inlet 24 and passage 23 to the working tip 14 passage 25 to withdraw the tissue fragmented by the work tip along with some of the treatment fluid.

Instruments of the type described above are often used in cataract surgery in which the eye lens is removed from the eye capsule and an intra-ocular lens (IOL) is then implanted. In such a procedure before the IOL is implanted it has been found to be desirable to cleanup lens substance and lens epithelial cells (LEC's) in the capsular bag of the eye and to remove them. Doing this procedure provides a more stable and long-term fixation for certain types of IOL's in the capsular bag. One manner of accomplishing the cleanup is to use a combination of irrigation of the capsular bag interior with a liquid together with the application of low power ultrasonic energy. This dislodges the unwanted cells and substances so that they can be removed from the capsular bag by the aspiration fluid flow.

In a cleanup procedure it is advantageous if the flow of the irrigation liquid can be made more directional than would be possible using the hand piece with the outer sleeve through which the liquid flows and exits from around the work tip that produces the ultrasonic energy. It is also better if the aspiration force is lower. As a result, typically a different tip from the one illustrated in FIG. 6, which breaks up the tissue, is used for the cleanup. In fact a completely different instrument called an infusion/aspiration (I/A) instrument is often used for this purpose. The I/A instrument has concentric infusion and aspiration lumens, but may have no ultrasonic vibration capability. Thus, when the phacoemulsification has been completed and cleanup is to be started, the surgeon must remove the phacoemulsification tool from the eye. Then the surgeon removes the first or phacoemulsification work tip, replaces it with a different cleanup work tip and then inserts the new work tip or a separate I/A tool in to the eye. This second insertion into the eye increases the possibilities of infection and trauma. Also, the A/I tool has a disadvantage in that the surgeon would have to keep inserting and withdrawing the ultrasonic work tip and the I/A tool from the eye. As a result, this would also subject the patient to the increased possibilities of infection and trauma.

As shown in the present inventor's own U.S. Pat. No. 7,083,589, the surgical instrument may be provided with a coupler body located between the connecting body and the work tip. In such a case the aspiration fluid flow is provided from the work tip aspiration passage through the coupler to an outlet without coming into contact with the interior of the connecting body. Irrigation fluid can be provided through a portion of the housing that surrounds the proximal part of the work tip so as to form a chamber which is in communication with a separate passage in the work tip. The coupler is detachably connected to the connecting body. This allows the removal of the work tip, which becomes a single use part, so that the rest of the instrument can be reused by replacing the work tip without having to sterilize the connecting body. However, the portion of the housing surrounding the work tip and which forms the chamber for irrigation fluid, also needs to be replaced in this design.

Accordingly a need exists for a surgical hand piece that can provide both ultrasonic energy to emulsify tissue, cells and other substances which are aspirated by an aspiration fluid and an irrigation liquid that can be applied to part of the operating site being cleaned in a more directional and controlled manner. Further, it would be beneficial if the cleaning were carried out by an A/I tool without ultrasonic vibration, but had a dual lumen structure to create different kinds of cleaning irrigation patterns and force. In addition, it would be beneficial if phacoemulsification instruments with dual lumens could have their operation varied without withdrawing the instrument from the eye and/or diverting the surgeon's attention from the operating site. This would reduce the chances of infection and trauma.

SUMMARY OF THE INVENTION

In accordance with the invention a surgical hand piece is provided that can perform all of the functions of emulsification of tissue and other substances by ultrasonic energy, aspiration of such tissue and substances, and/or provide a variable directed liquid irrigation of a site that is being worked on in order to clean up the site.

The invention provides a surgical phacoemulsification hand piece that has a novel work tip having a dual separate side-by-side lumen construction, as opposed to the concentric structure of the prior art. The work tip is effectively a unit of two tubes or sections of two tubes. Hereafter the term "tube" refers to a full tube or a section of a tube with each such tube or section having its own lumen. Where sections of tubes are used at least a portion of such sections are integrated along a common surface. One of the tubes receives the ultrasonic energy from the hand piece and its lumen forms the aspiration passage through which the emulsified tissue and other substances are removed. This tube can have any desired shape at its working end and any desired shape of aspiration opening. The irrigation liquid flows through the other tube and its end can have any number of openings or ports in any desired pattern to direct the flow of the irrigation fluid.

The novel work tip, whose lumens allow fluid to flow from proximal to distal ends and vice versa, permits switching of the tubes between aspiration and irrigation functions so that the surgeon has a work tip with different types of openings for both irrigation and aspiration functions. In different embodiments of the invention, both of the tubes of the work tip can be supplied with ultrasonic energy and either one used for aspiration or irrigation. Further, the tip may be designed so that it can be easily exchanged for a new tip and the hand piece put into service again without having to sterilize it.

The switching of the operation of the lumens can be achieved by manually switching the tubes connected to the irrigation supply and aspiration pump. However, this requires a stop in the procedure while the switch is made. As an alternative, it is proposed that the system have a rotating valve conveniently located on the housing of the aspiration pump. In one position the valve causes irrigation fluid to flow through one lumen and aspiration fluid to be withdrawn through the other. Operation of the valve causes the irrigation and aspiration fluid flow to switch lumens.

Another embodiment mounts the lumens in the hand piece so they can be manually rotated with respect to the inlet for the irrigation fluid and outlet for the aspiration fluids. Thus, by rotating a portion of the hand piece which the work tip is still located in the eye reverses the functions of the lumens. This is beneficial because it is fast and the surgeon does not have to take his or her attention away from the operation site.

The hand piece of the invention has numerous advantages. For example, the need for infusion sleeves within which the irrigation liquid flows is eliminated. An infusion sleeve is a separate item that needs to be attached to the instrument hand piece. This means that such sleeves have to be designed and manufactured for a particular hand piece. Also, the sleeves are subject to wear and tear and other complications. The elimination of the need for an infusion sleeve from the surgical hand piece has economic advantages in that there are fewer parts to deal with.

The hand piece of the present invention also has a surgical benefit in that it eliminates the need for the surgeon to remove a work tip from the operating site, such as the eye, and to insert a separate work tip or tips having irrigation/aspiration (1/A) capability, in order to perform special procedures, such as cortical and lens epithelial cleanup.

The principals utilized in the surgical hand piece can also be implemented in an UA tool design with two lumens, which may be side-by-side or concentric. The two lumens provide at least two different irrigation patterns for cleanup. By means of a mechanism within the hand piece, the irrigation and aspiration lines can be switched without having to remove the UA tool from the eye, and without the surgeon having to divert his attention from the eye, e.g., to operate a switching valve on the aspiration pump.

BRIEF DESCRIPTION OF THE DRAWINGS

The foregoing and other objects and advantage of the present invention will become more apparent upon reference to the following specification and annexed drawings in which:

FIGS. 3A, 3B, 3C and 3D are cross-sectional views showing various forms of integrated work tips;

FIGS. 4A and 4B are schematic views of a valve arrangement to control switching between irrigation and aspiration functions for the tubes of the work tip;

FIG. 12 is a plan view, partly in cross section, of a further embodiment of the surgical hand piece of the invention in which only the work tip and connecting body liners need to be replaced after use.

DETAILED DESCRIPTION OF THE INVENTION

Figure 1:
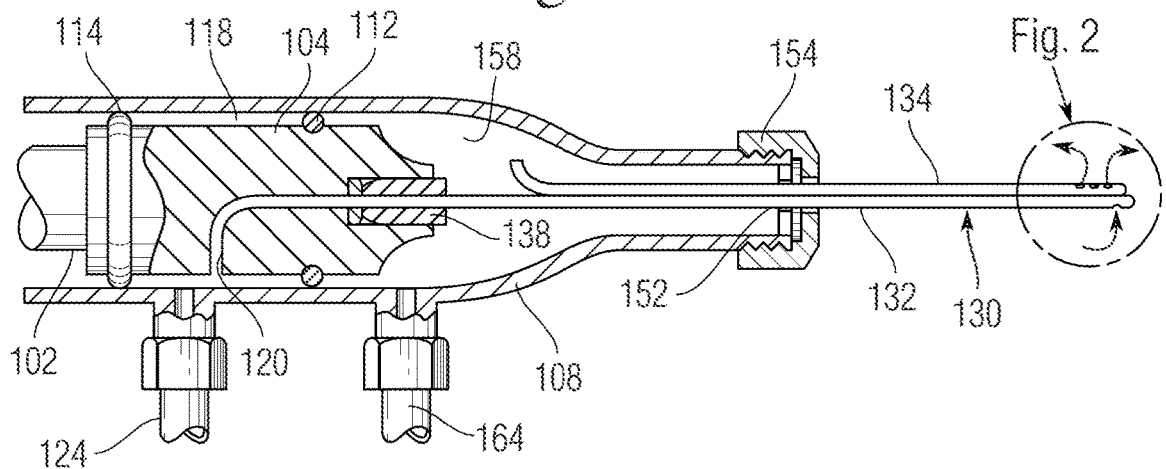
FIG. 1 is a plan view, partly in cross section, of one embodiment of the surgical hand piece of the invention.
Figure 6:
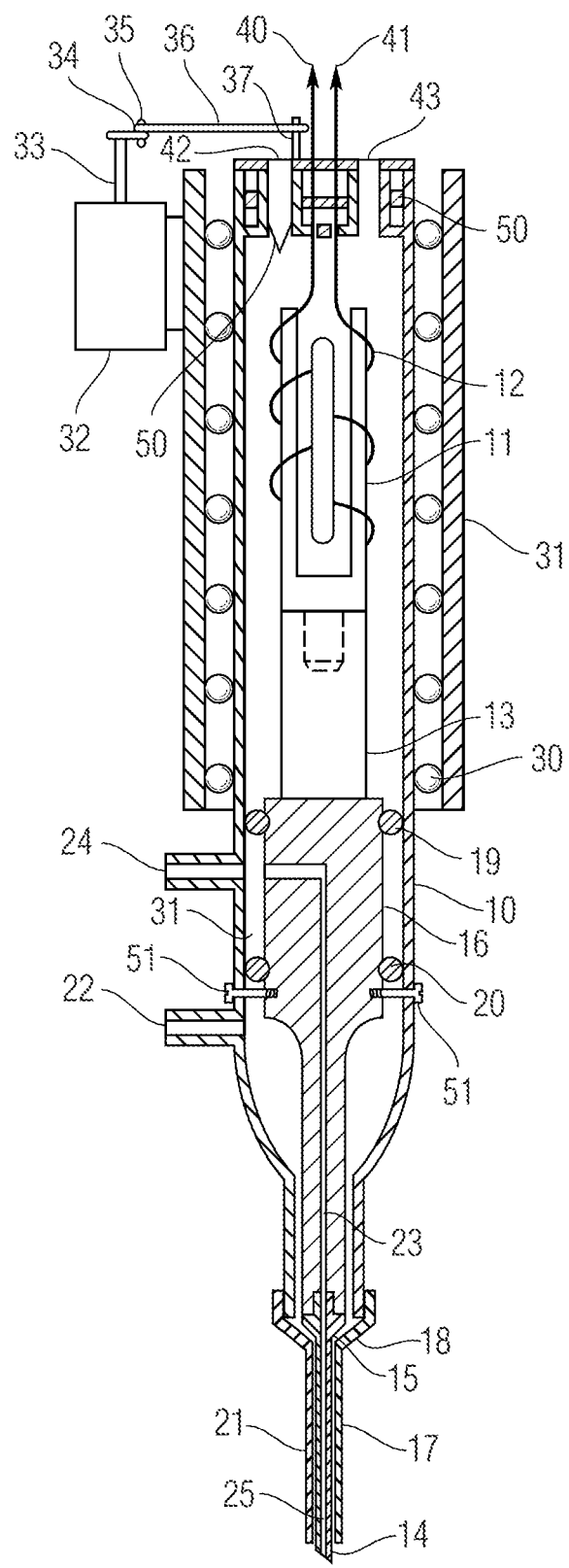
FIG. 6 is a view in cross-section of a prior art type of surgical hand piece.

FIG. 1 shows a first embodiment of the hand piece of the invention. It uses a number of the components of the prior art type of hand piece described above with respect to FIG. 6. The source of the electro-mechanical energy is shown schematically by reference number 102 and can be either the electromagnetic type as described or the piezoelectric type. It is preferred, and is conventional, that the output power of the source 102 can be controllably varied to set the ultrasonic power at the work tip distal end.

Connected to the source 102 is the connecting body 104 within a housing 108. A pair of O-rings 112 and 114 spaced apart around the connecting body 104 and engaging the inner surface of the housing form a first chamber 118. The first chamber 118 receives aspiration force from a line 124 that is connected to a suitable source such as a peristaltic pump. It is preferred that the negative (suction) pressure provided at line 124, be controllable. A flow passage 120 is formed in the connecting body 104 that communicates with the first chamber 118 and extends to the reduced diameter distal end of the connecting body 104.

A second chamber 158 is formed between the O-ring 112 and the distal end of the housing 108. This chamber receives irrigation fluid from a line 164 that is connected to a suitable source, such as a bag of saline solution or a liquid supply having a pump. Here also, it is preferred that the volume and pressure of the fluid be controllable. The proximal end of a work tip 130 extends through the distal end of the housing 108. A flange hub 152 is connected to an intermediate point of the work tip and the flange abuts against the distal end of the housing 108 and is held against it by a threaded collar 154. This forms a fluid tight seal at the distal end of the housing and seals the second chamber 158.

The work tip 130 is a unit of two tubes or tubular sections 132 and 134. The two tubes can be of any of the types illustratively shown in FIGS. 3A-3D and described below. As illustratively shown, the proximal end of the work tip 130 first tube 132 has a coupling 138 that is threaded into the distal end of the connecting body 104. This places the lumen of the first tube 132 in communication with the passage 120 in the connecting body 104. The tube 132 will also be provided with ultrasonic energy from the source 102 through the connecting body 104. At the proximal end of the work tip 130 there is a second tube 134, which is open, located in the housing second chamber 158 and in communication with any fluid in this chamber. With this arrangement, there is fluid flow to or from each of the tubes 132 and 134 of the integrated work tip 130. That is, aspiration, flow or liquid flow can be provided from the distal end of the first tube 132 through the passage 120 in the connecting body 104, into the first chamber 118 so as to exit at line 124 under suction from the aspiration pump. Similarly, irrigation fluid flow can be provided to line 164, to the second housing chamber 158, to the proximal end of the second tube 134 to exit at the distal end of tube 134.

Figure 1A:
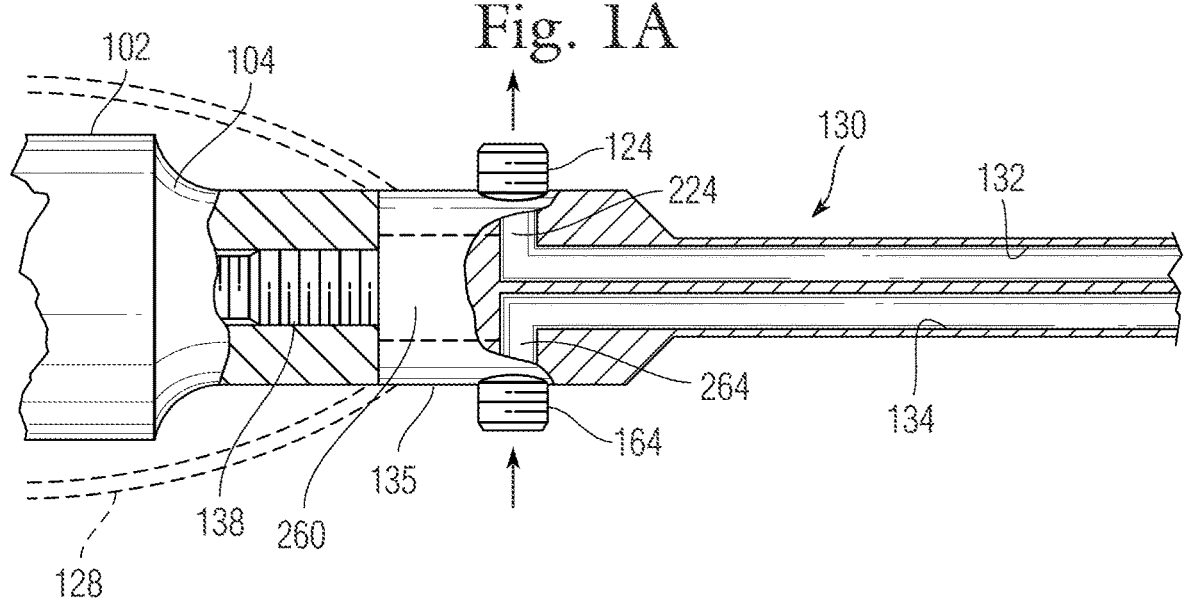
FIG. 1A is a plan view, partly in cross section, of another embodiment of the surgical hand piece of the invention.

FIG. 1A shows a further embodiment in which there is no flow passage in the connecting body 104. Here, the proximal end of the work tip 130 is a generally cylindrical hub 135 that receives the proximal ends of the tubes 132 and 134. The tubes can be any of the types described below with respect to FIGS. 3A-3D. The proximal end of the hub 135 is of reduced diameter so that it can be attached such as by threads 138 with threads in a recess of the distal end of the connecting body 104 whose proximal end is connected to the source of ultrasonic energy 102. The hub 135 has respective passages 224 and 264 to the lumen of each of the tubes 132 and 134. The aspiration and irrigation fluids are withdrawn or supplied, respectively, over the lines 124 and 164 through the hub passages directly to the lumens of the two tubes. The lines 124 and 164 can be inserted directly into the hub passages 224 and 264. A housing 128 (shown in dotted line) of a suitable shape is provided over the energy source 102 and the connecting body 104. In this embodiment, both tubes 132, 134 receive the ultrasonic energy. As described below, the fluids withdrawn from or supplied to the two tubes can be switched by using a control valve.

The work tip of FIG. 1A has an advantage in that there is no fluid flow through the connecting body 104 or any part of the instrument other than the hub 135 and work tip 130 itself. Therefore, they are the only parts of the instrument that can become contaminated if the patient being operated on has a malady such as "mad cow/prion" disease. Also, with this arrangement, while the housing may extend over the energy source 102 and the connecting body 104, it need not extend over the hub 135. Thus no fluid chamber is formed by the housing which needs to be exchanged after use. Only the work tip 130 and hub 135 have to be sterilized after each use of the instrument or they can be treated as "disposable" and a new work tip and hub can installed each time that the instrument is used. In order to make the disposability of the work tip more practical, it can be made, at least in part, of less expensive materials. For example, a core portion 260 of the hub (shown in dotted line) from connecting body 104 to the tubes 132, 134 and the tubes themselves may need to be made of a very hard material, e.g., titanium, in order to transmit vibrations of sufficient strength to affect the breakup of a cataract during its removal. However, a portion of the hub surrounding the core, the passages 224, 264 and the connectors 124, 164 may be made of a less expensive material, e.g., a hard plastic, in order to reduce its cost.

Figure 2:
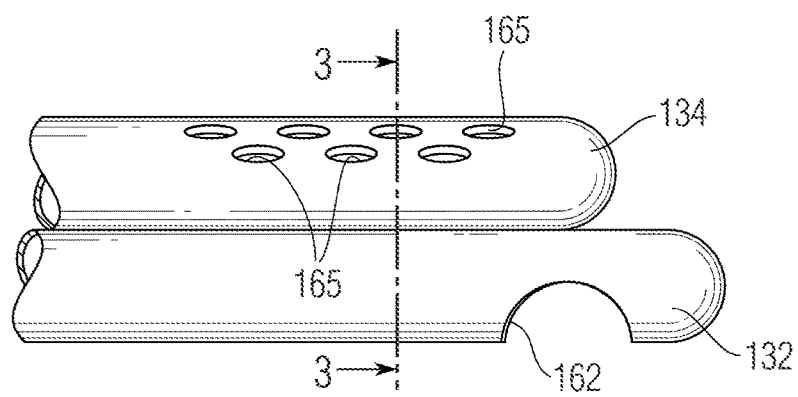
FIG. 2 is an enlarged view of the distal end of the work tip shown in FIG. 1.
Figure 5:
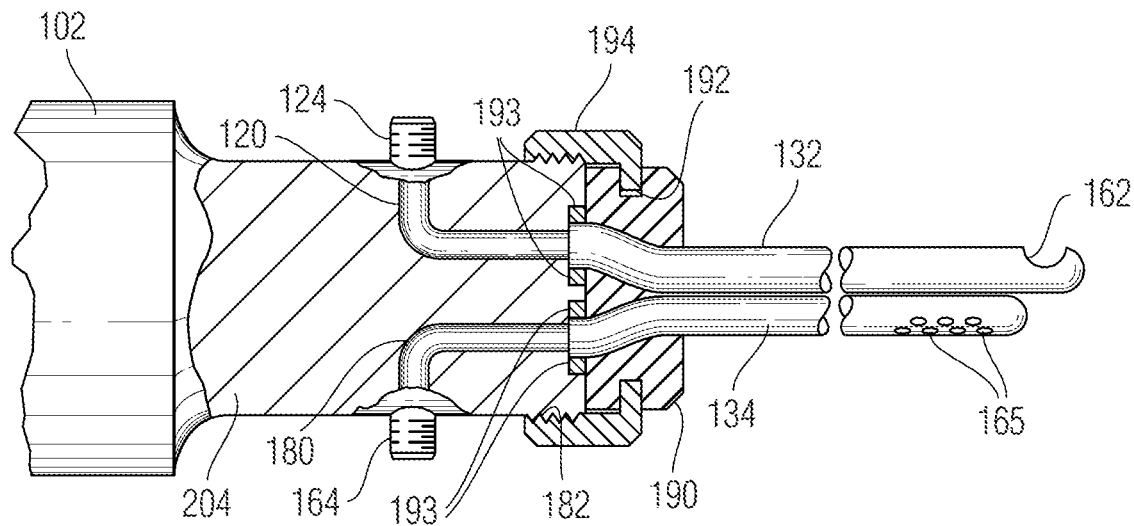
FIG. 5 is a view, partly in cross-section, of another embodiment of surgical hand piece according to the present invention.

FIG. 2 shows an illustrative example of the distal ends of the two tubes 132 and 134 of the work tip 130. The proximal ends of the tubes are disposed as shown in FIG. 1 or the inverse of what is shown in FIG. 1A or in another embodiment as shown in FIG. 5, or by any suitable arrangement such that ultrasonic energy from the transducer and aspiration fluid is coupled to the proximal end of at least one of the tubes and the proximal end of at least one tube can receive the irrigation fluid from its distal end. In this example the first tube 132 is intended to be connected to receive the ultrasonic energy from the source 102 and has a scooped, or concave shaped, opening 162 near its distal end to receive the emulsified tissue that is produced by vibrations of the free end of the tube. The opening 162 can be of any desired shape and size and also can be at the extreme distal end of the tube. The second tube 134 has at least one and preferably a plurality of openings 165 through which an irrigation liquid can flow to exit at the operating site. The number of openings 165 and their pattern can be selected as desired. There can be one or more rows along the tube length. The openings 165 in tube 134 preferably are oval (elliptical) in shape as shown. Oval shaped openings 165 allow for both good dispersion of the irrigation fluid and a large area for aspiration of cells and substances dislodged by the irrigation liquid. The openings 165 also can have the standard circular hole configuration. As explained below, the hand piece of the invention provides for switching of the functions to be performed by the two tubes. That is, either tube can be used to perform the irrigation function or the aspiration function.

FIGS. 3A, 3B, 3C and 3D show cross-sections of tubes that can be used for the work tip 130. In FIG. 3A two fully circular tubes 132a and 134a are joined together at the area 135, such as by welding, to form a unitary structure. The joining 135 can be continuous or spaced along the lengths of the two tubes. When two complete tubes are used for the work tip they do not necessarily have to be connected together along their lengths as shown in FIG. 3A since each tube has its own lumen and does not need any part in common with the other tube to have fluid flow therein. An arrangement of two separate tubes 132b and 134b is shown in FIG. 3B. A unitary structure work tip is formed by using a hub or a similar element to hold the two tubes together as shown in FIGS. 1, 1A and FIG. 5.

In FIG. 3C two half tube sections 132c and 134c are connected to a common central wall 137 to form a unitary structure. Here an overall somewhat elliptical tube can be divided into the two tube sections and then joined to the center common wall 137. In FIG. 3D there is a fully circular tube 134d on top of which a part of a circular tube section 132d is joined at 139 along its length, making the work tip a unitary structure. When two tube sections are used to form the work tip the proximal ends are modified (not shown) to have the appropriate shape, such as fully circular, so as to be able to perform its function such as coupling to the connecting body to receive ultrasonic energy and to receive aspiration and irrigation fluid. The distal ends also are modified to provide fluid flow from and to the aspiration and irrigation openings.

It should be understood that the two tubes 132 and 134 can be of different diameters and shapes in addition to the more symmetrical arrangements shown in the drawings. Also, the tubes can be made of any suitable material, such as titanium or any suitable material which can withstand the stress of vibration. Both tubes can be of the same material, or they can be of different materials. It also may be desirable to make one of the tubes, for example the one to which the irrigation fluid is usually applied, of a plastic material such as TEFLON®. While a tube of plastic material will not be able to vibrate if it receives ultrasonic energy, it can still be used to perform both the aspiration and irrigation functions depending upon which fluid is supplied to it. Further, the two tubes 132 and 134 can be of different lengths.

FIGS. 4A and 4B schematically show a valve arrangement for the supply lines 124 and 164. There is a valve 175 that receives one input from an irrigation liquid source, such as a bag of a saline solution using gravity feed or from a liquid source under controlled pressure and volume. The valve second input is from an aspiration source, such as a peristaltic pump, of controlled suction force or pressure. In FIG. 4A the valve 175 is in a position such that there is irrigation liquid flow is to line 164 meaning that there will be liquid in the second housing chamber 158 of FIG. 1 to be provided to the second tube 134 to flow out of its distal end. The aspiration source will be connected to the line 124 so that there will be negative pressure (suction) fluid in the first housing chamber 118 that is provided to the distal end of the first tube 132 through the passage 120 in the connecting body 104. Thus, fluid will flow from the distal end of tube 132 out of line 124 to the valve and then to the suction pump. As seen in FIG. 4B, by switching the valve 175 the conditions will be reversed so that there will be aspiration flow on line 164 causing the second tube 134 to perform an aspirating function and liquid flow in line 164 causing the first tube 132 to perform an irrigation function. Thus, the tubes 132, 134 are capable of fluid flow in either direction, depending on the function they are performing.

FIG. 5 shows another embodiment of the invention for coupling the work tip 130 to the hand piece. The same reference numbers are used for the same components of FIG. 1. Here there are two passages 120 and 180 in a connecting body 204. One end, the proximal end, of passage 120 is in communication with the irrigation fluid input of the supply line 124. The proximal end of passage 180 is in communication with the aspiration fluid of the supply line 164. The distal ends of the two passages 120 and 180 terminate at the distal end of the connecting body 204.

There are threads 182 around the connecting body distal end. A hub 190 is around the proximal ends of the work tip tubes 132 and 134 which are bent so that the proximal ends of their lumens are parallel to the distal ends of the connecting body passages 120 and 180. A collar 194 with internal threads on its open end has its flange end rotatably mounted in a groove 192 in the hub 190. There are mating index pieces, such as mating grooves and ribs or pins (not shown), on the opposing faces of the connecting body 204 distal end and the hub 190 so that the proximal end of the lumen of tube 132 will be aligned with the distal end of connecting body passage 120 and the proximal end of the lumen of tube 134 aligned with the distal end of passage 180. Other types of alignment pieces and markings can be used. When the tubes and connecting body are properly aligned the collar 194 is tightened on the connecting body threads 182 and the lumens at the proximal ends of tubes 132 and 134 will be brought into fluid communication with the distal ends of the connecting body passages 120 and 180. O-rings 193 are provided in the connecting body at the distal ends of passages 120 and 180 to make the communication fluid tight.

In this embodiment of the invention, both of the tubes 132, 134 receive the ultrasonic energy from the source 102. The valve 175 of FIG. 4 can be used with the hand piece of FIG. 5 to switch the fluid flow from the sources 124 and 164 to the lumens of tubes 132 and 134 of the integrated work tip. Since both tubes 132 and 134 receive ultrasonic energy the emulsification of tissue and its aspiration can take place through either one in addition to each tube being able to supply irrigation liquid through the different types and shapes of openings at the distal ends of the tubes.

A still further embodiment of a work tip for a hand piece according to the present invention is shown in FIG. 12. As seen in FIG. 12 the connecting body 204 has passages 120, 180 as in the embodiment of FIG. 5. However, in FIG. 12 the connecting body has a narrow section 205 on which there are the threads 182. Tubes 132 and 134 abut this narrow section of the connecting body. A threaded collar 195 is slide over the tubes and engages the threads 182. The narrow portion 205 of the connecting body and the tubes have alignment pieces (not shown) so that passages 120, 180 are aligned with the lumens in the tubes 132, 134. Further, the tubes 132, 134 have proximal flanges that fits within the collar 195 so that when the collar is tightened onto the threads 182 of the narrow part 205 of the connecting body, a tight stable connection is made between the tubes and body.

Plastic disposable tubes 324, 364 are provided. These disposable tubes can be inserted into the passages 120, 180 until their distal ends enter the two work tip tubes 132, 134. As a result, the tubes are made of a flexible material so that they can bend along the passages 120, 180. The proximal ends of tubes 132, 134 have O-rings or other sealing type openings which are made of a material softer than the disposable tubes so that these tubes can push through the seals into the tubes 132, 134 and form a fluid tight connection with them. Such seals can be of the type shown in FIG. 5, except they are located in the tubes 132, 134, instead of the connecting piece 204. The ends of the disposable tubes have connector 325, 365 at their proximal ends for connection to the source of irrigation fluid or aspiration vacuum.

When the hand piece is used in its intended fashion and the procedure is over, the hand pieces can be quickly readied for use on another patient without the need for sterilization. In particular, the collar 195 is loosened. Then the working tip with tubes 132, 134 is disposed of. In addition, tubes 324, 364 are also disposed of. Each of these sets of tubes is replaced with clean, pre-sterilized tubes, and the hand piece is ready for the next use. This is possible because the only parts of the hand piece that come into contact with the aspiration fluid from the patient are the interiors of the tubes 132, 134 and 324, 364. As noted with respect to the embodiment of FIG. 5, it may be useful in terms of expense to make the tubes 132, 134 of a material that is hard, but not as expensive as titanium, so as to be able to transmit the vibration force. The tubes 324, 364 do not have to transmit the vibration force, so they can readily be made of a plastic material such as TEFLON®, as a way of reducing the cost of the disposable parts of the hand piece.

The work tips of the invention, such as illustratively shown in FIGS. 1, 1A, 5 and 12, can be used with only an irrigation/aspiration (I/A) function. That is, the source of ultrasonic energy can be turned off and only the aspiration and irrigation fluids supplied to the tubes 132 and 134. Also, the aspiration force is lowered, e.g., from 500 mm Hg to 5-10 mm Hg during the cleaning operation so that the posterior capsule tissue at the back of the eye is not drawn into the tube. Here also the valve arrangement of FIG. 4 can be used so that either of the tubes can receive aspirated tissue or supply irrigation fluid. However, it may be preferable to utilize the tube with the small circular holes 165 for this cleaning procedure, again to avoid aspirating the posterior capsule tissue. Thus, the same instrument can be used for the phacoemulsification function while performing irrigation and aspiration as an operation takes place and also only for I/A functions (no ultrasonic energy is used) useful for cleaning the capsular bag as described above. This eliminates the need for the surgeon changing instruments and also provides the surgeon with a working tip having two tubes with different shape openings available for both aspiration and irrigation.

Figure 7:
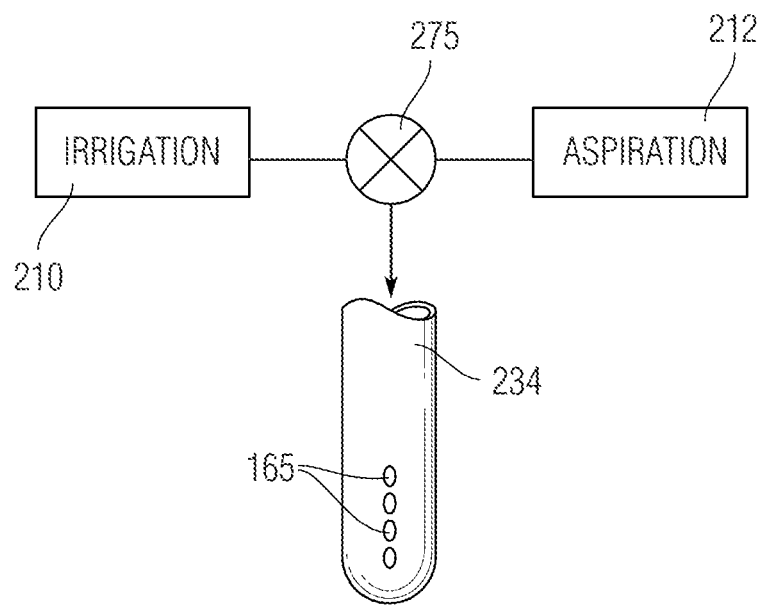
FIG. 7 is a schematic view of a modification of the work tip according to the present invention.

Following the above, only one of the tubes can be used only as an I/A working tip. That is, it does not receive ultrasonic energy. This is shown in FIG. 7 in which the tube 234 follows the general format of the tube 134 of FIG. 2. That is, it has the oval openings 165 along the tube length. It receives either irrigation or aspiration fluid from sources 210 and 212 at its proximal end through a valve 275. The tube 234 can be used alone in the eye capsular bag for the substance and cell cleanup procedure described above. The oval shaped openings 165 allow for both good dispersion of the irrigation fluid and a large area for aspiration of cells and substances dislodged by the irrigation liquid.

In each of the embodiments described a support member can be mounted around the work tip 130 to rest against the eye when the work tip is inserted in the eye. For example, a cannula can be inserted into the incision site and then the work tip 130 can be placed into the cannula. This cannula provides • thermal insulation at the incision sight in order to protect the eye from any heat generated by the vibration of work tip 130. This arrangement is shown in FIG. 8.

As noted above, FIG. 1A illustrates a surgical hand piece with a single use work tip 130. FIG. 8 is a schematic side view of the eye 300 of a patient showing the dual lumen work tip 130 (not to scale) positioned to enter a surgical opening made in the cornea 302 of the eye during a procedure to remove cataracts 304 from the eye by phacoemulsification. The work tip enters the eye through a cannula 310 adapted to fit in the opening. Once in the vicinity of the cataract, the ultrasonic vibration of the work tip 130 causes the cataract to break up into small pieces which can be aspirated through one of the tubes 132, 134. In addition to the pieces of cataract, some of the fluid in the eye is also removed during the aspiration. If too much fluid is removed, the cornea can collapse, complicating the procedure and possibly damaging the eye. As noted above, fluid can be replaced by injecting it into the other tube of the work piece.

Figure 9:
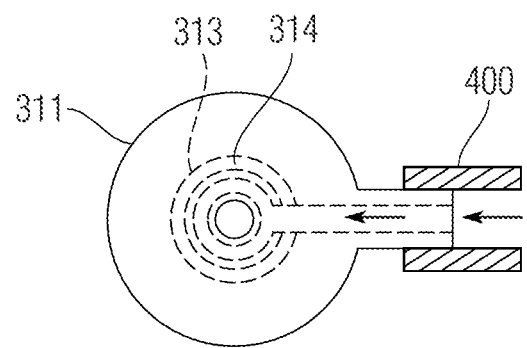
FIG. 9 is a top view of the cannula of FIG. 8.

The cannula is generally cylindrical in shape. As best seen in the top view of FIG. 9, the cannula has a large outer flange 311 which keeps it from completely entering the eye. Also, it has a small flange or protrusions 313 on the part adjacent the interior surface of the cornea in order to anchor the cannula in place between the two flanges. These small protrusions or flanges are located circumferentially around the cylindrical shape and must not be too large because they are pressed into the opening in the cornea and stretch it slightly as they enter the eye. However, they do not stretch it so much that it damages the corneal tissue surrounding the opening.

Figure 8:
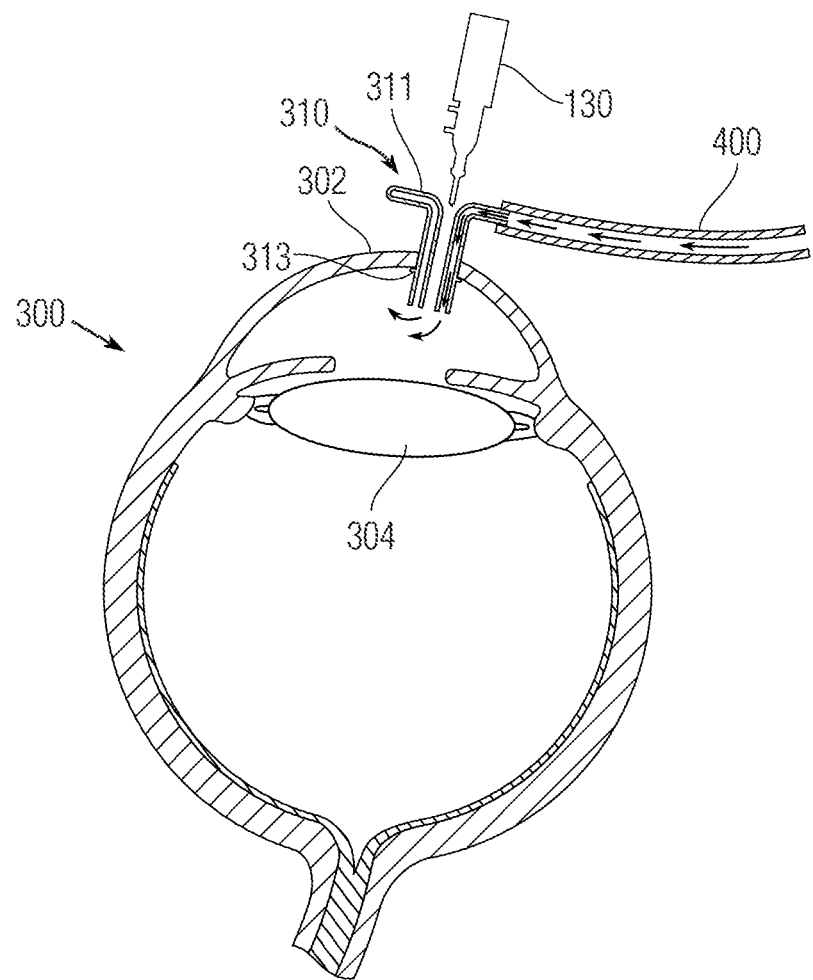
FIG. 8 is a schematic side view of the eye showing a cannula located in the cornea and a dual lumen work tip positioned to enter the cannula.
Figure 10:
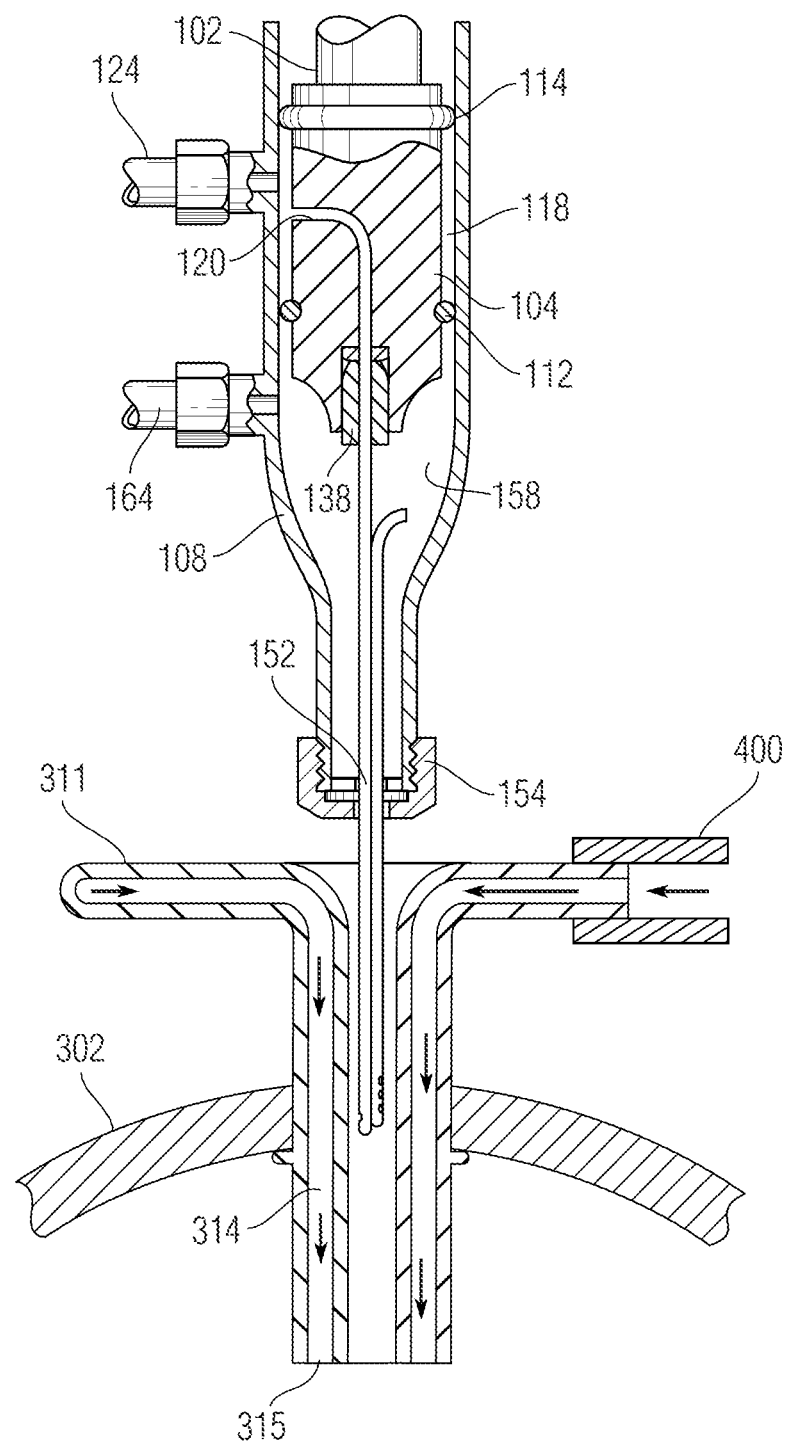
FIG. 10 is an enlarged cross sectional view of the cannula positioned in the cornea and receiving auxiliary infusion fluid which passes through it and into the eye.

The housing 128 for the surgical piece as shown in FIG. 1A, as is also depicted in FIGS. 8 and 10. Housing 128 covers the source of the electro-mechanical energy 102 and the connecting body 104. However, the work tip 130 is not within the housing, which facilitates easy exchange of work tips. As a result, the ultrasonically vibrating work tip 130 is exposed. The cannula 310 protects the corneal tissue surrounding the opening from friction caused by this vibration. In order to assist in friction reduction the cannula can be made of a low friction material such as TEFLON®.

Figure 11A:
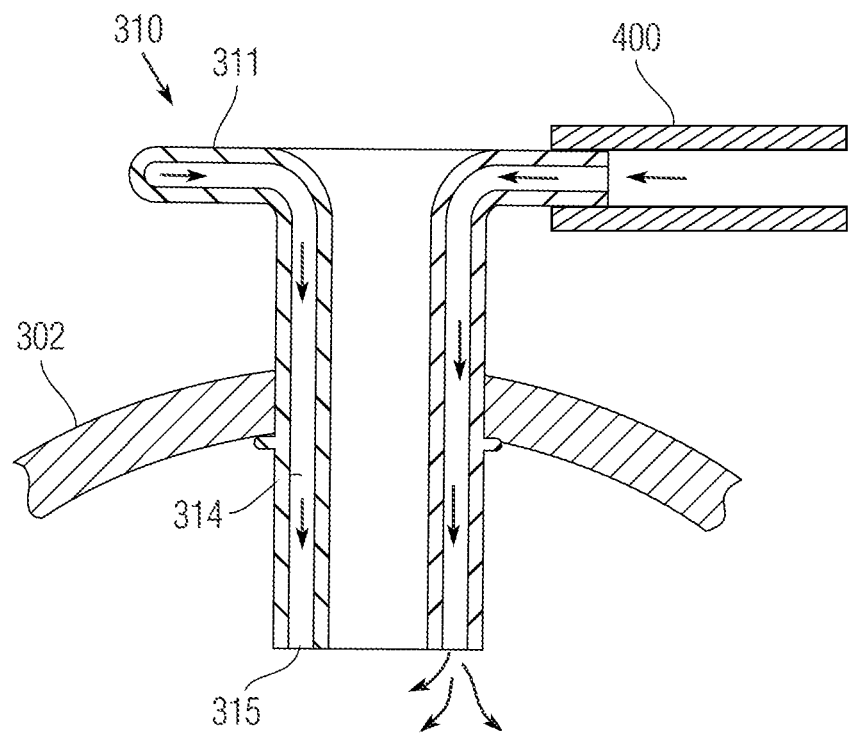
FIGS. 11A and 11B show alternative auxiliary infusion fluid flow paths in the cannula of FIG. 8.
Figure 11B:
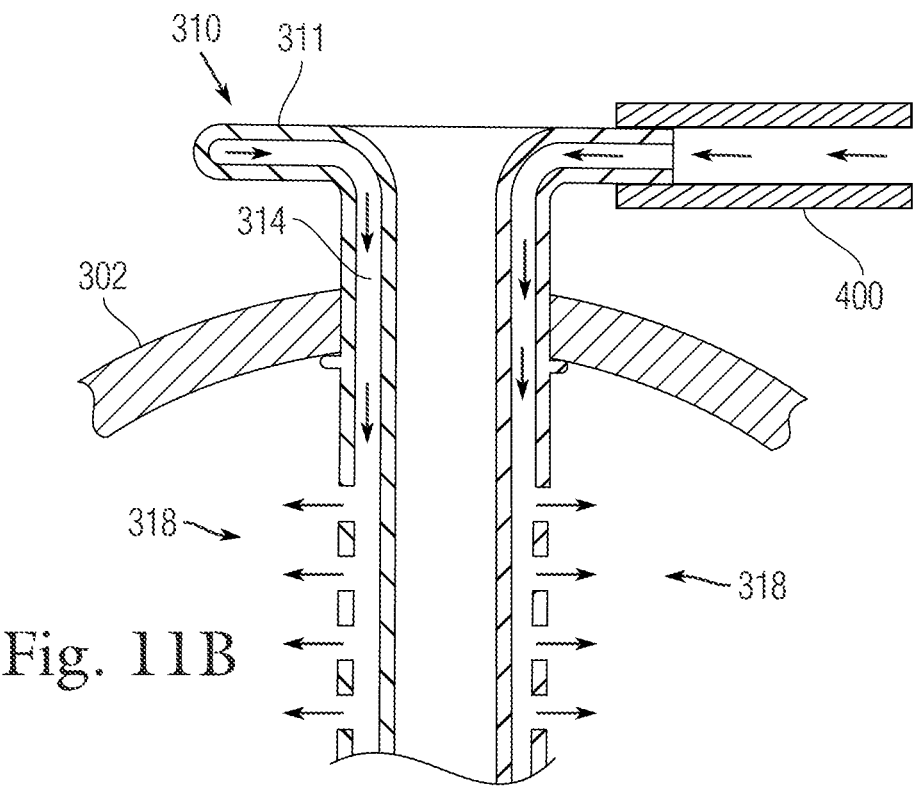

In order to further protect the cornea from the heat generated by friction from the vibrating work piece, the cannula can be provided with cooling fluid as shown in FIG. 8 and in more detail in enlarged FIG. 10. The cannula 310 can be connected to an infusion line 400. Within the cannula there is a cylindrical channel 314 so that the fluid from line 400 completely surrounds the interior of the cannula and cools its outer surface, which engages the cornea 302. The fluid can exit the cannula within the eye as auxiliary irrigation fluid though a circular exit 315 as best shown in FIG. 11A. However, as an alternative or in addition to the circular exit 315 there may be provided a series of holes 318 as shown in FIG. 11B.

If the infusion fluid from the work tip 130 is too little, it can be compensated for by the auxiliary fluid infused through the cannula. If the amount is too much, either because of the work tip and/or the cannula, the central opening in the cannula through which the work tip extends is sufficiently wide that the work tip does not block it and the extra fluid can pass out of the eye around the work tip.

While the invention has been shown and described in connection with the removal of cataract from the eye of a patient, the apparatus and method may also be used for other types of surgery in other parts of the body, e.g., the removal of neurological tissue.

Specific features of the invention are shown in one or more of the drawings for convenience only, as each feature may be combined with other features in accordance with the invention. Alternative embodiments will be recognized by those skilled in the art and are intended to be included within the scope of the claims. Accordingly, the above description should be construed as illustrating and not limiting the scope of the invention. All such obvious changes and modifications are within the patented scope of the appended claims.

I claim:

1. A surgical hand piece comprising:
   a source of ultrasonic energy;
   a connecting body having a proximal end connected to said ultrasonic energy source and a distal end; and
   a work tip having a proximal hub from which extend at least first and second tubes aligned side by side and adjacent to each other, said hub having first and second external openings, each of said tubes having a proximal end connected to separate passages in said hub leading to the external openings, said work tip being detachably connected to said connecting body distal end and being of a material suitable for conveying the ultrasonic energy from said ultrasonic energy source to the distal end of said tubes, wherein ultrasonic energy may be transmitted from said source of ultrasonic energy through said connecting body to said hub in order to ultrasonically vibrate both said at least first and second tubes,
   wherein each of said at least first and second tubes has a lumen that is to receive or discharge a fluid at its proximal end from one of first and second fluid sources that are respectively irrigation and aspiration fluids, the lumen of each of said at least first and second tubes being separate and spaced apart, and each tube of said at least first and second tubes having an opening at its distal end through which the fluid received at or discharged from the proximal end of the respective lumen of each tube of said at least first and second tubes exits from or enters the tube, with each said tube distal end opening being separate, independent of, spaced from and without being in communication with the distal end opening of the other tube, aspiration fluid flow being in one of said at least first and second tubes and irrigation fluid flow being in the other, and said aspiration and irrigation fluid flows being selectively and alternately reversible in said tubes.

2. The surgical hand piece according to claim 1 wherein the first and second external openings are on opposite sides of the hub and are at an angle to the respective tubes.

3. The surgical hand piece according to claim 1 further including a valve to receive the fluids from the first source and discharge fluid to the second source and for switching the received and discharged fluids respectively to be supplied to or received from the respective lumen of either one of said at least first and second tubes, wherein the respective lumen of each of said at least first and second tubes can receive or discharge the fluid from either one of said first and second sources as switched by said valve.

4. The surgical hand piece according to claim 1 wherein one of the at least first and second tubes has a distal opening that is larger than the distal opening of the other.

5. The surgical hand piece according to claim 4 wherein the tube with the larger distal opening has a single opening with a concave shape and the tube with the other distal opening has a plurality of small oval shaped openings.

6. The surgical hand piece according to claim 1 wherein said work tip is detachably connected to said connecting body distal end by a threaded connection.

7. The surgical hand piece according to claim 1 wherein said at least first and second tubes have about the same diameter and nearly the same length after leaving the hub to facilitate their being used for either aspiration or irrigation.

* * * * *